(12) United States Patent
Valet et al.

(10) Patent No.: US 9,381,229 B2
(45) Date of Patent: Jul. 5, 2016

(54) PHARMACEUTICAL COMPOSITION FOR USE IN THE TREATMENT OF DYSFUNCTION ASSOCIATED WITH AGING

(71) Applicants: INSERM (INSTITUT NATIONAL DE LA SANTE ET DE LA RECHERCHE MEDICALE), Paris (FR); UNIVERSITE PAUL SABATIER TOULOUSE III, Toulouse (FR)

(72) Inventors: Philippe Valet, Toulouse (FR); Cedric Dray, Toulouse (FR); Claude Knauf, Toulouse (FR); Oksana Kunduzova, Toulouse (FR); Isabelle Castan-Laurell, Toulouse (FR)

(73) Assignees: INSERM (INSTITUT NATIONAL DE LA SANTE ET DE LA RECHERCHE MEDICALE), Paris (FR); UNIVERSITE PAUL SABATIER TOULOUSE III, Toulouse (FR)

( * ) Notice: Subject to any disclaimer, the term of this patent is extended or adjusted under 35 U.S.C. 154(b) by 0 days.

(21) Appl. No.: 14/360,958

(22) PCT Filed: Nov. 27, 2012

(86) PCT No.: PCT/EP2012/073743
§ 371 (c)(1),
(2) Date: May 28, 2014

(87) PCT Pub. No.: WO2013/079487
PCT Pub. Date: Jun. 6, 2013

(65) Prior Publication Data
US 2015/0290286 A1    Oct. 15, 2015

(30) Foreign Application Priority Data
Nov. 28, 2011 (EP) .................... 11306573

(51) Int. Cl.
| | |
|---|---|
| *A61K 38/16* | (2006.01) |
| *A61K 38/10* | (2006.01) |
| *A61K 38/00* | (2006.01) |
| *A01N 43/40* | (2006.01) |
| *A01N 43/16* | (2006.01) |
| *A61K 38/17* | (2006.01) |
| *B60G 21/055* | (2006.01) |
| *C12Q 1/68* | (2006.01) |
| *G01N 33/68* | (2006.01) |

(52) U.S. Cl.
CPC .......... *A61K 38/1709* (2013.01); *B60G 21/055* (2013.01); *B60G 21/0551* (2013.01); *C12Q 1/6883* (2013.01); *G01N 33/6893* (2013.01); *B60G 2202/135* (2013.01); *B60G 2204/122* (2013.01); *B60G 2204/1224* (2013.01); *B60G 2204/14* (2013.01); *B60G 2206/11* (2013.01); *B60G 2206/427* (2013.01); *C12Q 2600/118* (2013.01); *C12Q 2600/158* (2013.01); *G01N 2333/47* (2013.01); *G01N 2800/50* (2013.01)

(58) Field of Classification Search
None
See application file for complete search history.

(56) References Cited

U.S. PATENT DOCUMENTS

| | | | | |
|---|---|---|---|---|
| 7,947,280 | B2 * | 5/2011 | Ashley ............... | A61K 38/1709 424/185.1 |
| 8,946,382 | B2 * | 2/2015 | Cuttitta .................. | C07K 14/47 530/326 |
| 2005/0075275 | A1 | 4/2005 | Albrecht et al. | |
| 2005/0112701 | A1 | 5/2005 | Arndt et al. | |
| 2008/0182779 | A1 | 7/2008 | Ashley et al. | |
| 2010/0221255 | A1 | 9/2010 | Cuttitta et al. | |

FOREIGN PATENT DOCUMENTS

| | | |
|---|---|---|
| EP | 1 967 210 A1 | 9/2008 |
| WO | 2007/026356 A2 | 3/2007 |
| WO | 2009/033819 A2 | 3/2009 |
| WO | 2009/043504 A2 | 4/2009 |

OTHER PUBLICATIONS

Ashley et al. 2005. 65:73-82.*
Berry et al. 2004. Circulation 110(II):187-193.*
Klein et al. Pharm. and Therap. 107:198-211.*
Frier et al 2009. Am. J. Phys. Regul. Integr. Comp. Physiol. 297:R1761-1768.*
Chabi et al. 2008. Aging Cell. 7:2-12.*
Simpkin et al., "Apelin-13 and apelin-36 exhibit direct cardioprotective activity against ischemia-reperfusion injury"; Basic Research in Cardiology, Aug. 13, 2007, pp. 518-528, vol. 102, No. 6, Steinkopff-Verlag, DA.
Goetze et al., "Apelin: A new plasma marker of cardiopulmonary disease", Regulatory Peptides, Jan. 15, 2006, pp. 134-138, vol. 133, No. 1-3, Elsevier Science BV, NL.
Dai et al., "Apelin increases contractility in failing cardiac muscle", European Journal of Pharmacology, Dec. 28, 2006, pp. 222-228, vol. 553, No. 1-3, Elsevier Science, NL.
Rong-Rong et al., "Apelin suppresses apoptosis of human vascular smooth muscle cells via APJ/PI3-K/Akt signaling pathways", Amino Acids, May 22, 2010, pp. 1193-1200, vol. 39, No. 5, Springer-Verlag, VI.

* cited by examiner

*Primary Examiner* — Shulamith H Shafer
(74) *Attorney, Agent, or Firm* — Whitham, Curtis & Cook, P.C.

(57) ABSTRACT

The present invention relates to an APJ receptor agonist or an apelinomimetic for use in the treatment or the prevention of a dysfunction associated with aging.

1 Claim, 13 Drawing Sheets

Figure 5:
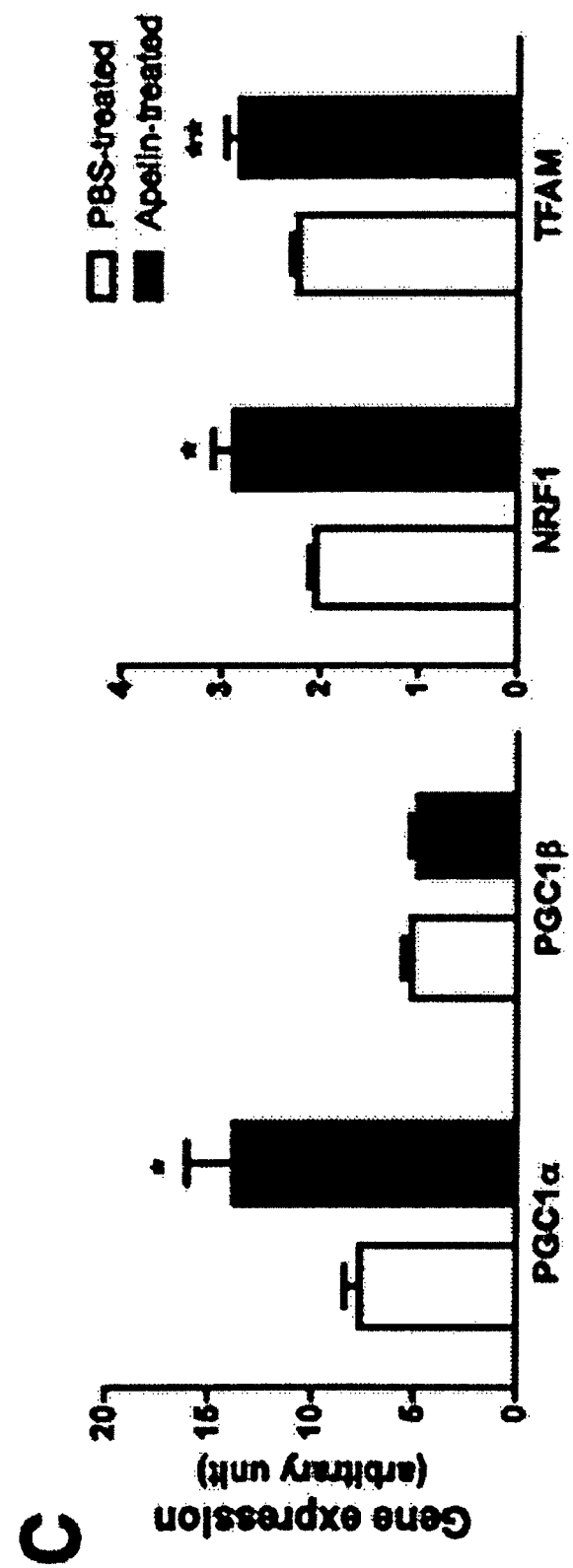
Figure 5:
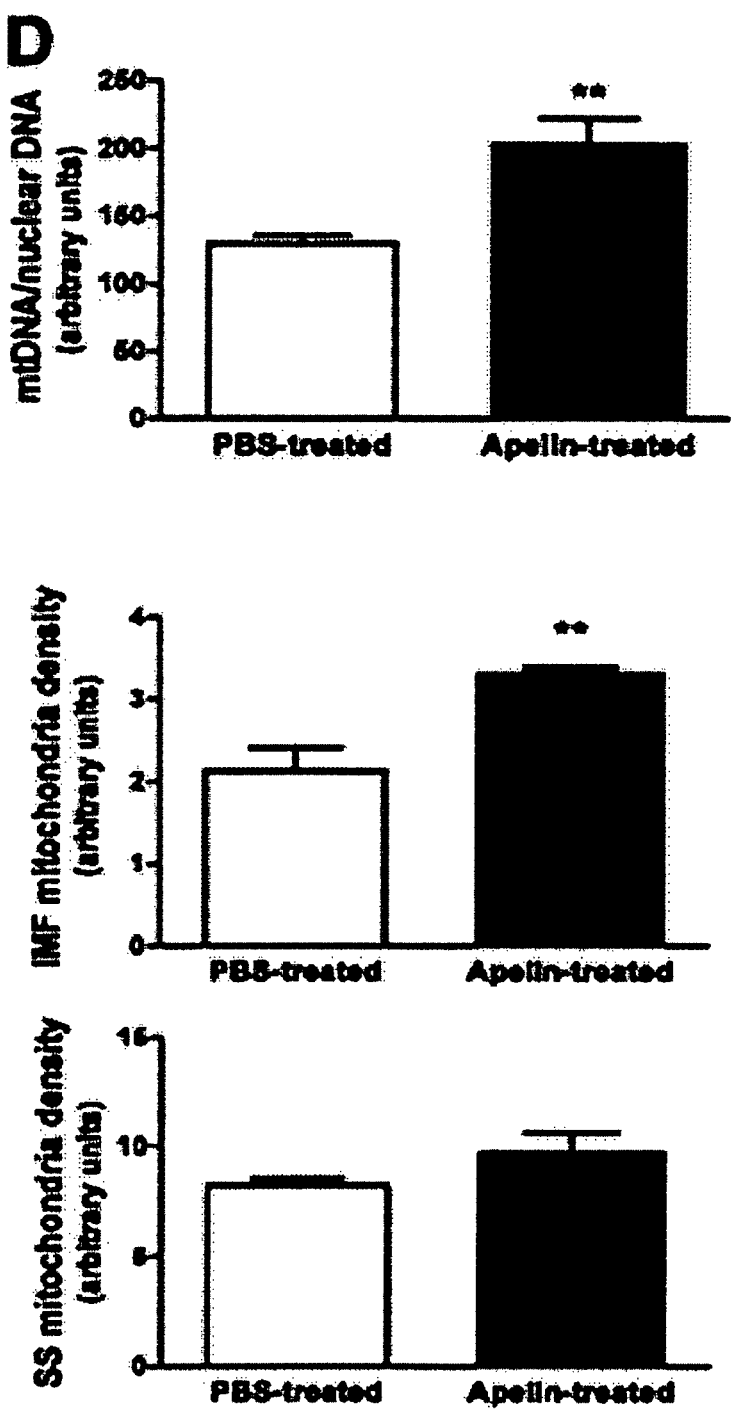
Figure 5:
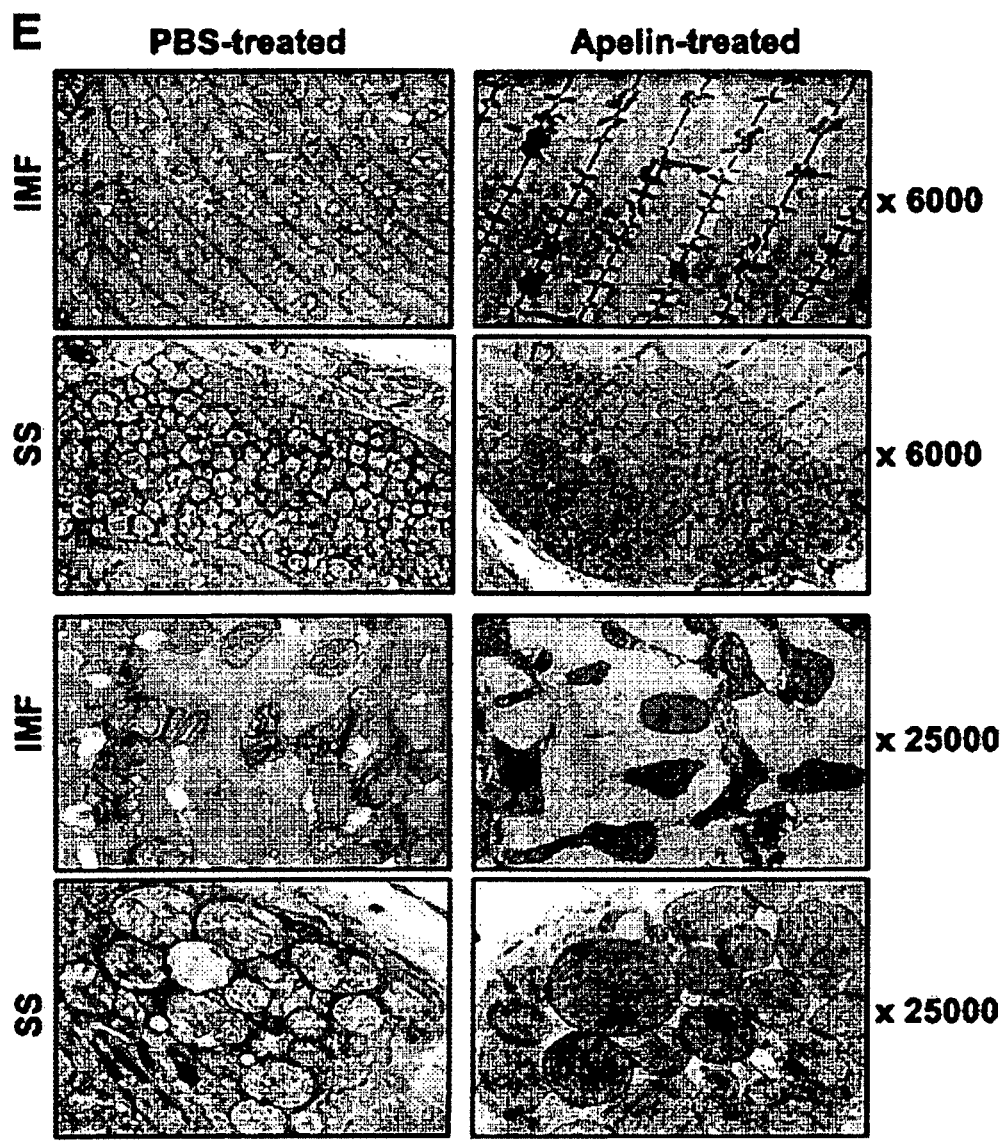

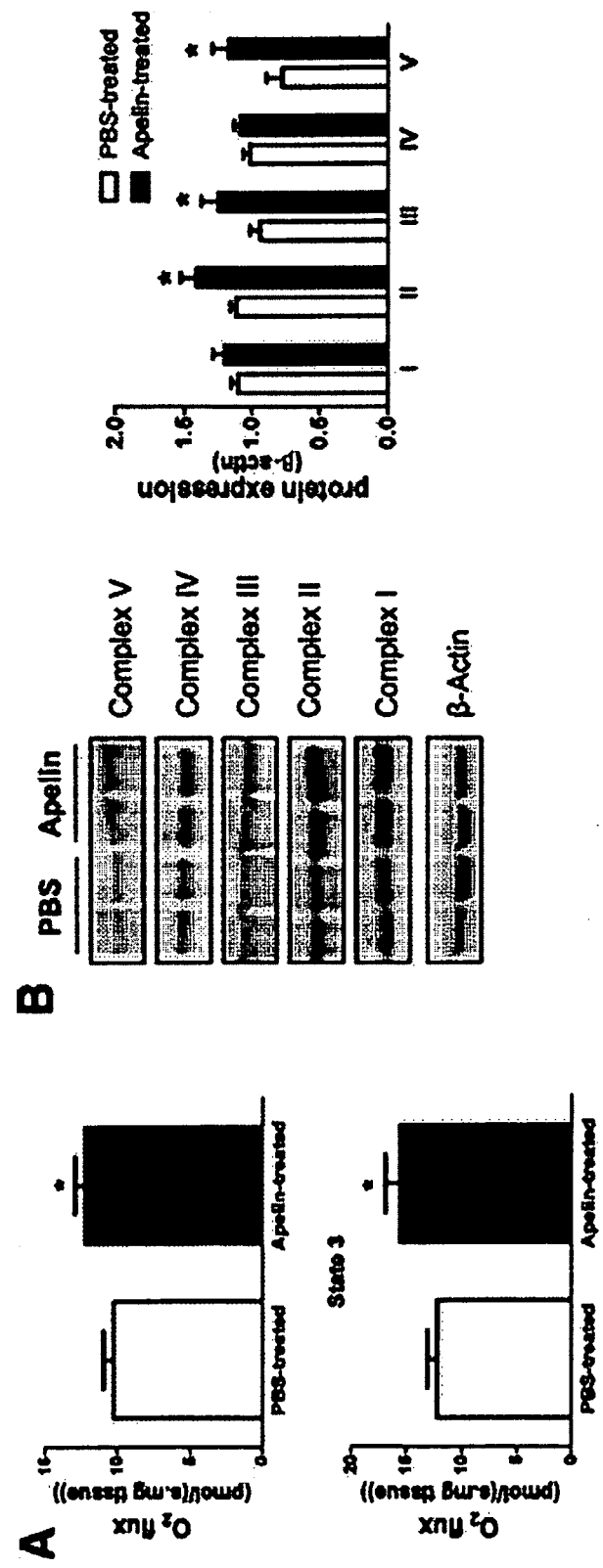
Figure 5 A and B

Figure 6:
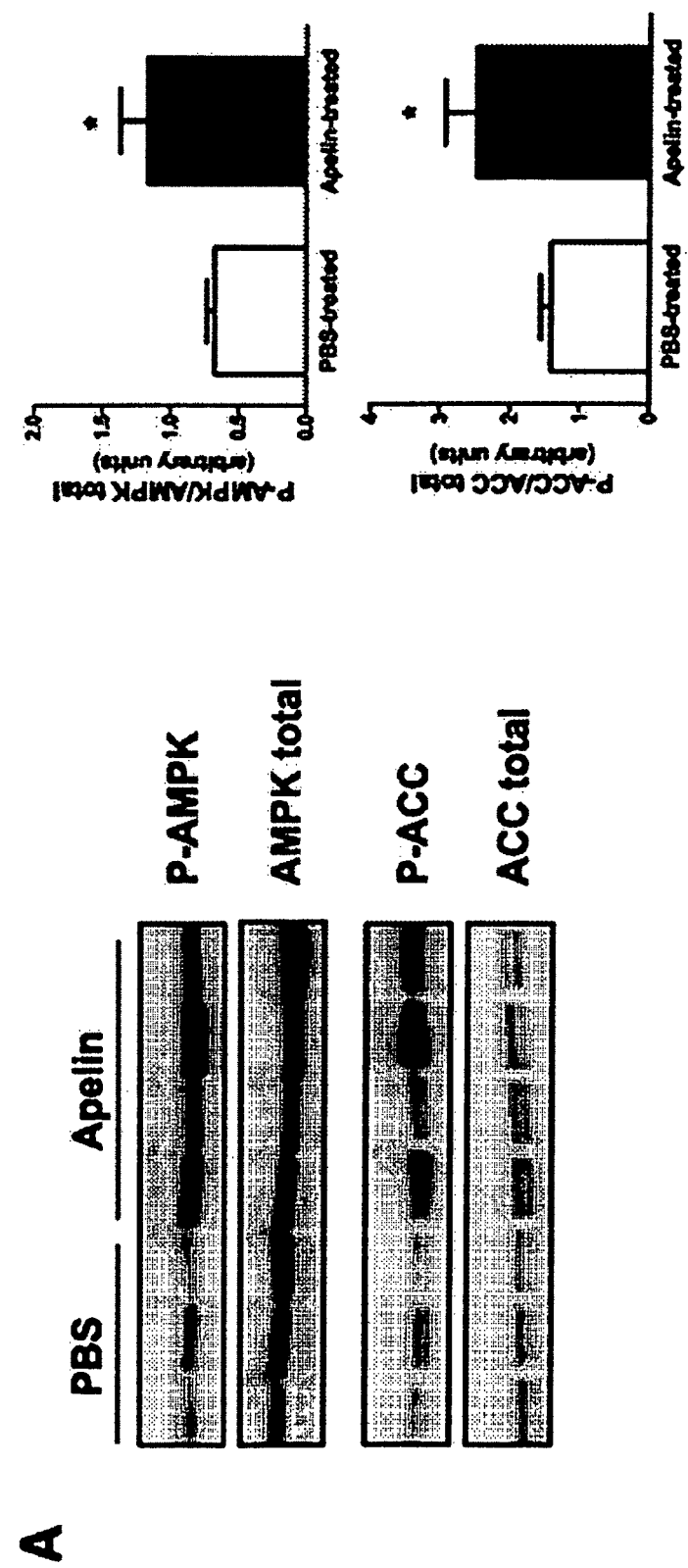
Figure 6:
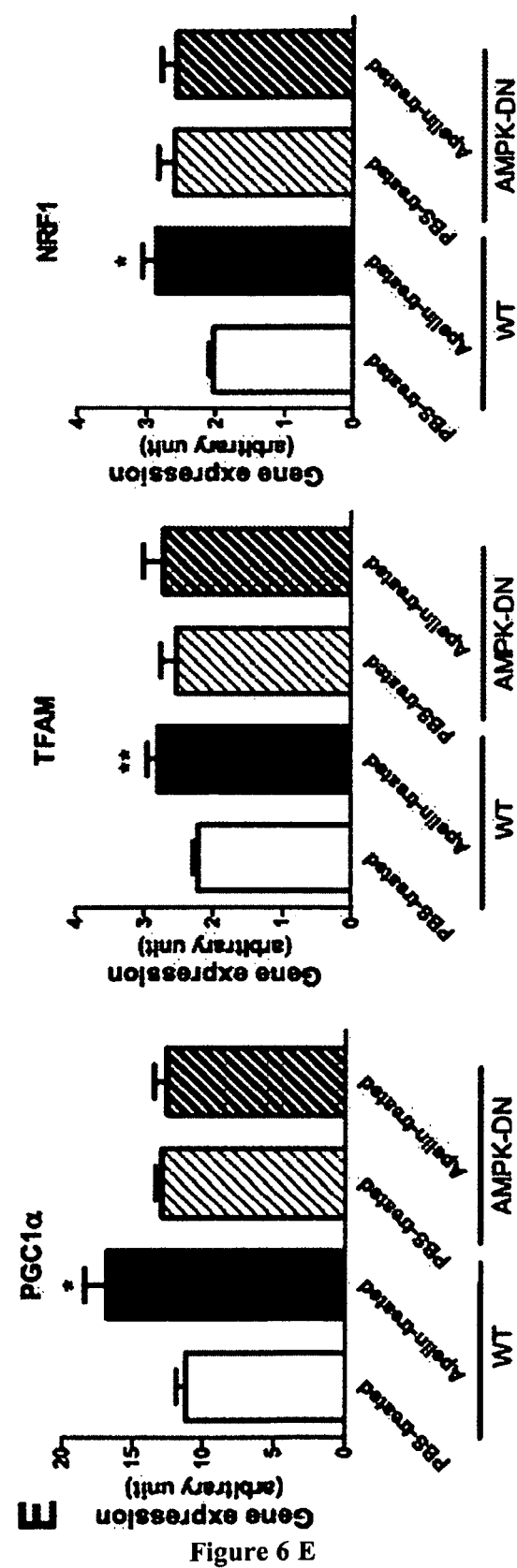

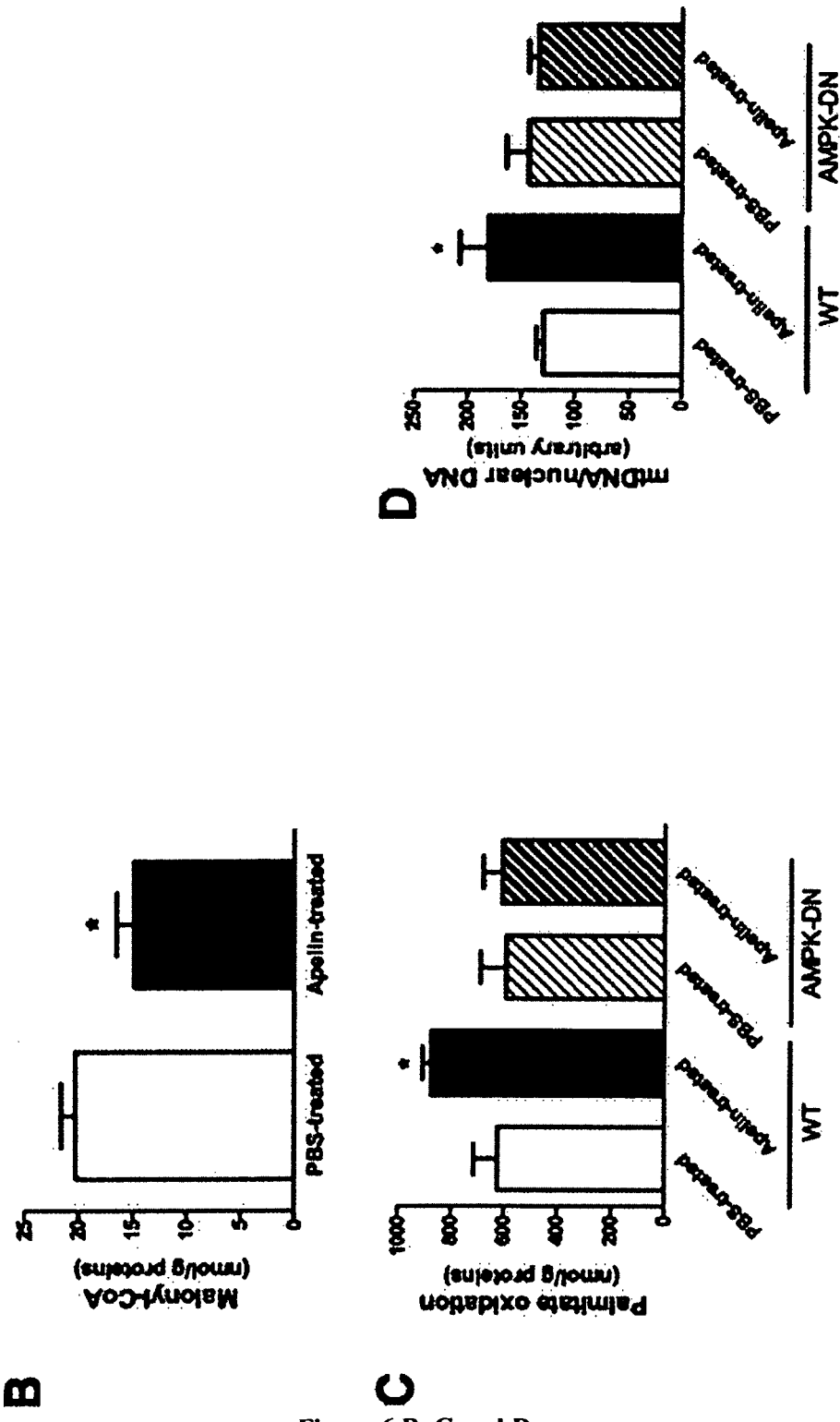
Figure 6 B, C and D ved as an adipocyte-secreted factor (Boucher et al, Endocrinology, 2005), apelin was known to exert several central and peripheral effects in different tissues such as the regulation of the cardiovascular, immune and gastrointestinal functions but also in fluid homeostasis, angiogenesis, proliferation of different cell types and embryonic development (see for example US2008/0182779, US2010/0221255 or US2005/0075275). However its role in dysfunctions associated with aging has not yet been identified.

PHARMACEUTICAL COMPOSITION FOR USE IN THE TREATMENT OF DYSFUNCTION ASSOCIATED WITH AGING

FIELD OF THE INVENTION

The present invention relates to an APJ receptor agonist or an apelinomimetic for use in the treatment or the prevention of a dysfunction associated with aging.

BACKGROUND OF THE INVENTION

Dysfunctions related to age can be defined as the age-related loss of function of organs in people. Lot of dysfunctions can appear in the brain and be responsible in part of degenerative diseases but also in muscles. In this case, people with dysfunctions of their muscle suffer of sarcopenia.

Sarcopenia can be defined as the age-related loss of muscle mass, strength and function (Waters, Baumgartner & Garry 2000; Vandervoort & Symons 2001). Although there is no specific level of lean body mass or muscle mass at which one can say sarcopenia is present (Roubenoff 2001), any loss of muscle mass is of importance because there is a strong relationship between muscle mass and strength (Roth, Ferrell & Hurley 2000). Sarcopenia appears to begin in the fourth decade of life and accelerates after the age of approximately 75 years (Waters, Baumgartner & Garry 2000). With aging and inactivity, the most atrophy is seen in the fast twitch (FT) fibers which are recruited during high-intensity, anaerobic movements. Although sarcopenia is mostly seen in physically inactive individuals, it is also evident in individuals who remain physically active throughout their lives. This finding suggests that physical inactivity is not the only contributing factor to sarcopenia. Current research is finding that the development of sarcopenia is a multifactorial process. Many factors, including physical inactivity, motor-unit remodeling, decreased hormone levels, and decreased protein synthesis; may all contribute to sarcopenia.

Although sarcopenia may be partly reversible with appropriate exercise interventions, there is a need to find original treatment of sarcopenia.

Apelin is a peptide, identified as the endogenous ligand of APJ, an ubiquitously expressed G protein coupled receptor (Tatemoto K, Hosoya M, Habata Y, Fujii R, Kakegawa T, Zou M X, Kawamata Y, Fukusumi S, Hinuma S, Kitada C, Kurokawa T, Onda H, Fujino M. Isolation and characterization of a novel endogenous peptide ligand for the human APJ receptor. Biochem Biophys Res Commun. October 251(2): 471-6. 1998). Apelin is synthesized as a 77-amino acid prepropeptide that is cleaved in different fragments including apelin-36, apelin-17, apelin-13 and the post-translationally [Pyr1] apelin-13 with a conversion of the N-terminal glutamate to pyroglutamate preventing enzymatic breakdown and thus preserving biological activity (Tatemoto K, Hosoya M, Habata Y, Fujii R, Kakegawa T, Zou M X, Kawamata Y, Fukusumi S, Hinuma S, Kitada C, Kurokawa T, Onda H, Fujino M. Isolation and characterization of a novel endogenous peptide ligand for the human APJ receptor. Biochem Biophys Res Commun. October 251(2):471-6. 1998). Before to be revealed as an adipocyte-secreted factor (Boucher et al,

SUMMARY OF THE INVENTION

The inventors show that apelin plays a role in energy metabolism and particularly in energetic mechanisms in mitochondria. They show that apelin treatment increases complete fatty acid oxidation (FAO), glucose transport, mitochondrial oxidative capacity and biogenesis in muscle of insulin-resistant mice. Furthermore, they show that skeletal muscle appears as the major tissue target for apelin action, where it mediates increased fuel consumption. Thus apelin could be used in diseases related to problems in energetic mechanism in mitochondria.

Using apelin KO mice and wild type mice chronically-treated by apelin, the inventors identified that markers of sarcopenia like myostatin and myogenin were respectively down or up regulated in old mice. Thus, apelin should be used to treat dysfunction associated with aging and particularly in sarcopenia.

In this context, apelin could contribute to improve the energetic mechanism in mitochondria of muscles or other mitochondria-altered tissues (heart, brain, . . . ) and thus contribute to improve the performance of deficient and frail muscles or other age-associated deficient tissues. Thus, apelin may be used in the treatment or prevention of sarcopenia or in the treatment or prevention of frailty syndrome. Apelin may be also used in the treatment or prevention of progeria also known as Hutchinson-Gilford Progeria Syndrome.

Thus, a first object of the invention relates to an APJ receptor agonist or an apelinomimetic for use in the treatment or the prevention of a dysfunction associated with aging.

Another object of the invention relates to an ex vivo method for predicting the ability to a patient to be affected by a dysfunction associated with aging, comprising the step consisting of detecting apelin expression in a sample obtained from said patient.

DETAILED DESCRIPTION OF THE INVENTION

APJ Receptor Agonist or Apelinomimetic and Uses Thereof

A first object of the invention relates to an APJ receptor agonist or an apelinomimetic for use in the treatment or the prevention of a dysfunction associated with aging.

As used herein, the term "dysfunction associated with aging" denotes mitochondrion alterations (number and/or function) leading to metabolic dysfunctions observed in elderly and increased with aging leading to age-related diseases such as loss of muscle mass (sarcopenia), of heart efficacy, neurodegeneration.

In a preferred embodiment, the dysfunction associated with aging may be a dysfunction of brain like Alzheimer disease, Parkinson disease or Huntington disease or a dysfunction of muscle.

In another preferred embodiment, the dysfunction of muscle may be a dysfunction a skeletal muscle or cardiac muscle like chronic or acute heart failure.

In still another preferred embodiment, the compounds according to the invention are used for the treatment of sarcopenia.

In still another preferred embodiment, the compounds according to the invention are used for the treatment or the prevention of the frailty syndrome. In still another preferred embodiment, the compounds according to the invention are used for the treatment or the prevention of progeria.

The term "APJ receptor" intends the receptor for apelin originally identified by O'Dowd et al. (O'Dowd et al, 1993, Gene 136: 355360).

As used herein the term "APJ receptor agonist" refers to any compound, natural or not, capable of promoting the APJ receptor function. Examples of the APJ receptor agonists of the present invention include but are not limited to polypeptides, antibodies, aptamers and small organic molecules.

Agonistic activities of a test compound toward APJ receptor may be determined by any well known method in the art. For example, since the agonist of the present invention can promote the function of the APJ receptor, the agonist can be screened using the natural agonist of APJ receptor (i.e. apelin) and its receptor. Typically, the agonist of the present invention can be obtained using the method screening the substance promoting the function of the APJ receptor, which comprises comparing (i) the case where apelin is brought in contact with the APJ receptor and (ii) the case where a test compound is brought in contact with the APJ receptor. In the screening method of the present invention, for example, (a) the binding amounts of apelin to the APJ receptor are measured (i) when apelin is brought in contact with the APJ receptor and (ii) apelin and a test compound are brought in contact with the APJ receptor; and comparing the results; or, (b) cell stimulating activities (e.g., the activities that promote arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH changes, etc.) mediated by the APJ receptor are measured (i) when apelin is brought in contact with the APJ receptor and (ii) a test compound is brought in contact with the APJ receptor; and comparing the results. Typically, the test compounds that provide a higher promotion or at least the same promotion of APJ receptor than apelin are then selected as APJ receptor agonists. Specific examples of the screening method of the present invention include: (1) a method of screening the substance promoting the function of the APJ receptor, which comprises measuring the binding amounts of labeled apelin to the APJ receptor when the labeled apelin is brought in contact with the APJ receptor and when the labeled apelin and a test compound are brought in contact with the APJ receptor; and comparing the amounts; (2) a method of screening the substance promoting the function of the APJ receptor, which comprises measuring the binding amounts of labeled apelin to a cell containing the APJ receptor or a membrane fraction of the cell, when the labeled apelin is brought in contact with the cell or membrane fraction and when the labeled apelin and a test compound are brought in contact with the cell or membrane fraction, and comparing the binding amounts; and, (3) a method of screening the substance promoting the function of the APJ receptor, which comprises measuring the binding amounts of labeled apelin to the APJ receptor expressed on a cell membrane by culturing a transformant having a DNA encoding the APJ receptor, when the labeled apelin is brought in contact with the APJ receptor and when the labeled apelin and a test compound are brought in contact with the APJ receptor, and comparing the binding amounts. In those examples, the test compounds that provide a higher binding or at least the same binding as apelin are then selected as APJ receptor agonists. Specifically, a method for determining whether a compound is an APJ receptor agonist is described in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Galzi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). The US Patent Application Publication N° US 2005/0112701 also described test system for the identification of a ligand for angiotension receptor like-1 (APJ receptor) comprising an APJ receptor. Another method is also described in the US Patent Publication U.S. Pat. No. 6,492,324.

In one embodiment, the APJ receptor agonist is a small organic molecule. The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

Examples of small organic molecules that are APJ receptor agonists include those described in the European Patent Application Publication N° EP19030052 and in Iturrioz X. et al. (Iturrioz X, Alvear-Perez R, De Mota N, Franchet C, Guillier F, Leroux V, Dabire H, Le Jouan M, Chabane H, Gerbier R, Bonnet D, Berdeaux A, Maigret B, Gaizi J L, Hibert M, Llorens-Cortes C. Identification and pharmacological properties of E339-3D6, the first nonpeptidic apelin receptor agonist. FASEB J. 2010 May; 24(5):1506-17. Epub 2009 Dec. 29). Typically, a small organic molecule that is an APJ receptor agonist has the general formula (I):

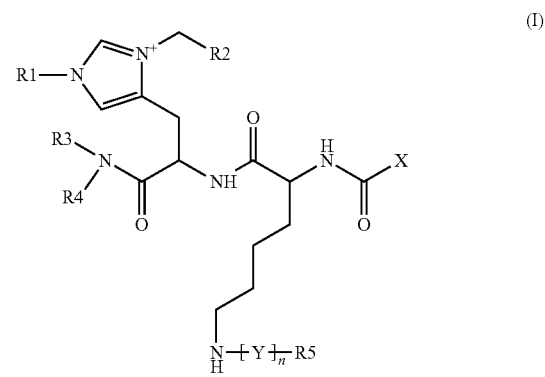

wherein:

R1 is an aryl, alkylaryl, heteroaryl or alkylheteroaryl group.

R2 is a hydrogen atom or an aryl group

R3 and R4 represent a hydrogen atom or a heterocycloalkyl group providing that R3 and R4 cannot represent simultaneously a hydrogen and that R3 and R4 can both be part of a heterocycloalkyl group R5 represents a group selected from the group consisting of boc, fmoc, texas red, patent blue V, lissamine, and rhodamine 101 n is an integer from 0 to 1

Y represents $-CO-(NH)_{n'}$-A-NH— group with:

n' is an integer from 0 to 1

A is a group selected from the group consisting of:

—$(CH_2)_{n''}$—

—$[(CH_2)_2-O]_{n'''}-(CH_2)_2$—

—$(CH_2)_m$—NH—CO—$(CH_2)_{m'}$—

—$(CH_2)_m$—NH—CO—$(CH_2)_{m'}$—NH—CO—$(CH_2)_{m''}$—

—$(CH_2)_m$—CO—NH—$(CH_2)_{m'}$—

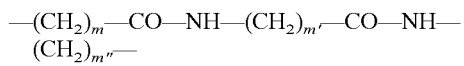

with n" representing an integer from 1 to 20
with n'" representing an integer from 1 to 10
with m, m' and m" representing independently from the other an integer from 1 to 15
X represents a group chosen in the following list:

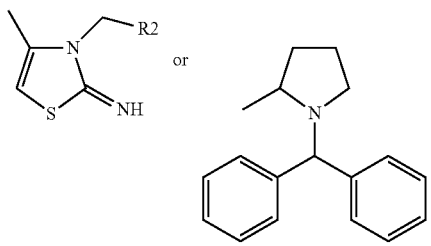

Alternatively, the APJ receptor agonist may consist in an antibody (the term including "antibody portion").

In one embodiment of the antibodies or portions thereof described herein, the antibody is a monoclonal antibody. In one embodiment of the antibodies or portions thereof described herein, the antibody is a polyclonal antibody. In one embodiment of the antibodies or portions thereof described herein, the antibody is a humanized antibody. In one embodiment of the antibodies or portions thereof described herein, the antibody is a chimeric antibody. In one embodiment of the antibodies or portions thereof described herein, the portion of the antibody comprises a light chain of the antibody. In one embodiment of the antibodies or portions thereof described herein, the portion of the antibody comprises a heavy chain of the antibody. In one embodiment of the antibodies or portions thereof described herein, the portion of the antibody comprises a Fab portion of the antibody. In one embodiment of the antibodies or portions thereof described herein, the portion of the antibody comprises a F(ab')$_2$ portion of the antibody. In one embodiment of the antibodies or portions thereof described herein, the portion of the antibody comprises a Fc portion of the antibody. In one embodiment of the antibodies or portions thereof described herein, the portion of the antibody comprises a Fv portion of the antibody. In one embodiment of the antibodies or portions thereof described herein, the portion of the antibody comprises a variable domain of the antibody. In one embodiment of the antibodies or portions thereof described herein, the portion of the antibody comprises one or more CDR domains of the antibody.

As used herein, "antibody" includes both naturally occurring and non-naturally occurring antibodies. Specifically, "antibody" includes polyclonal and monoclonal antibodies, and monovalent and divalent fragments thereof. Furthermore, "antibody" includes chimeric antibodies, wholly synthetic antibodies, single chain antibodies, and fragments thereof. The antibody may be a human or nonhuman antibody. A nonhuman antibody may be humanized by recombinant methods to reduce its immunogenicity in man.

Antibodies are prepared according to conventional methodology. Monoclonal antibodies may be generated using the method of Kohler and Milstein (Nature, 256:495, 1975). To prepare monoclonal antibodies useful in the invention, a mouse or other appropriate host animal is immunized at suitable intervals (e.g., twice-weekly, weekly, twice-monthly or monthly) with antigenic forms of APJ. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or QuilA, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

Briefly, the antigen may be provided as synthetic peptides corresponding to antigenic regions of interest in APJ. Following the immunization regimen, lymphocytes are isolated from the spleen, lymph node or other organ of the animal and fused with a suitable myeloma cell line using an agent such as polyethylene glycol to form a hydridoma. Following fusion, cells are placed in media permissive for growth of hybridomas but not the fusion partners using standard methods, as described (Coding, Monoclonal Antibodies: Principles and Practice: Production and Application of Monoclonal Antibodies in Cell Biology, Biochemistry and Immunology, 3$_{rd}$ edition, Academic Press, New York, 1996). Following culture of the hybridomas, cell supernatants are analyzed for the presence of antibodies of the desired specificity, i.e., that selectively bind the antigen. Suitable analytical techniques include ELISA, flow cytometry, immunoprecipitation, and western blotting. Other screening techniques are well-known in the field. Preferred techniques are those that confirm binding of antibodies to conformationally intact, natively folded antigen, such as non-denaturing ELISA, flow cytometry, and immunoprecipitation.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The Fc' and Fc regions, for example, are effectors of the complement cascade but are not involved in antigen binding. An antibody from which the pFc' region has been enzymatically cleaved, or which has been produced without the pFc' region, designated an F(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FR1 through FR4) separated respectively by three complementarity determining regions (CDR1 through CDR5). The CDRs, and in particular the CDR5 regions, and more particularly the heavy chain CDR5, are largely responsible for antibody specificity.

It is now well-established in the art that the non CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody.

This invention provides in certain embodiments compositions and methods that include humanized forms of antibodies. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3 A of the CDRs in a three dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible, as long as they would not abrogate the ability of the antibody to bind a given antigen. Suitable human immunoglobulin molecules would include IgG1, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *J. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

Thus, as will be apparent to one of ordinary skill in the art, the present invention also provides for F(ab') 2 Fab, Fv and Fd fragments; chimeric antibodies in which the Fc and/or FR and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

The various antibody molecules and fragments may derive from any of the commonly known immunoglobulin classes, including but not limited to IgA, secretory IgA, IgE, IgG and IgM. IgG subclasses are also well known to those in the art and include but are not limited to human IgG1, IgG2, IgG3 and IgG4.

In another embodiment, the antibody according to the invention is a single domain antibody. The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In another embodiment the APJ receptor agonist is an aptamer.

Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996). Then after raising aptamers directed against APJs as above described, the skilled man in the art can easily select those promoting APJ receptor function.

In another embodiment the APJ receptor agonist may consist in a polypeptide. Preferably, said polypeptide is the apelin itself. More preferably, the polypeptide is an apelin polypeptide.

The term "apelin" has its general meaning in the art and includes naturally occurring apelin and function conservative variants and modified forms thereof. The apelin can be from any source, but typically is a mammalian (e.g., human and non-human primate) apelin, and more particularly a human apelin. The sequence of apelin protein and nucleic acids for encoding such proteins are well known to those of skill in the art. Apelin is synthesized as 77-amino acid precursor and is found as a dimer, stabilized by disulfide bridges (Lee D K, Saldivia V R, Nguyen T, Cheng R, George S R, O'Dowd B F. Modification of the terminal residue of apelin-13 antagonizes its hypotensive action. Endocrinology. January 146(1):231-6. 2005). The pre-apelin is converted by proteolytic cleavage to produce different C-terminal fragments, including apelin-36, apelin-17, apelin-13, and the post-translationally modified ($Pyr^1$)apelin-13, all are agonist to apelin receptor: APJ. The lack of cysteine residues in these C-terminal fragments suggests that the mature peptides are monomeric. It should be understood that, as those of skill in the art are aware of the sequence of these molecules, any apelin protein or gene sequence variant may be used as long as it has the properties of an apelin.

"Function conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, most preferably at least 85%, and even more preferably at least 90%, and which has the same or substantially similar properties or functions as the native or parent protein to which it is compared.

According to the invention the term "apelin" polypeptide refers to any polypeptide that comprises the apelin-13 C-terminal fragment. Accordingly, the term encompasses apelin itself or fragments thereof comprising the apelin-17 or apelin-36 fragments.

In specific embodiments, it is contemplated that apelin polypeptides used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain.

Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa).

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the apelin polypeptides described herein for therapeutic delivery.

According to the invention, apelin polypeptides may be produced by conventional automated peptide synthesis methods or by recombinant expression. General principles for designing and making proteins are well known to those of skill in the art.

Apelin polypeptides of the invention may be synthesized in solution or on a solid support in accordance with conventional techniques. Various automatic synthesizers are commercially available and can be used in accordance with known protocols, apelin polypeptides of the invention may also be synthesized by solid-phase technology employing an exemplary peptide synthesizer such as a Model 433A from Applied Biosystems Inc. The purity of any given protein; generated through automated peptide synthesis or through recombinant methods may be determined using reverse phase HPLC analysis. Chemical authenticity of each peptide may be established by any method well known to those of skill in the art.

As an alternative to automated peptide synthesis, recombinant DNA technology may be employed wherein a nucleotide sequence which encodes a protein of choice is inserted into an expression vector, transformed or transfected into an appropriate host cell and cultivated under conditions suitable for expression as described herein below. Recombinant methods are especially preferred for producing longer polypeptides.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Those of skill in the art are aware of various techniques for optimizing mammalian expression of proteins. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below. Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

In the recombinant production of the apelin polypeptides of the invention, it would be necessary to employ vectors comprising polynucleotide molecules for encoding the apelin-derived proteins. Methods of preparing such vectors as well as producing host cells transformed with such vectors are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect genes. Examples of regulatory sequences include transcriptional promoters, operators, or enhancers, mRNA ribosomal binding sites, and appropriate sequences which control transcription and translation.

The terms "expression vector," "expression construct" or "expression cassette" are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in EP-A-0367566; and WO 91/18982.

In general, the vectors useful in the invention include, but are not limited to, plasmids, phagemids, viruses, other vehicles derived from viral or bacterial sources that have been manipulated by the insertion or incorporation of the antisense oligonucleotide, siRNA, shRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are well known in the art.

Preferred viruses for certain applications are the adenoviruses and adeno-associated (AAV) viruses, which are double-stranded DNA viruses that have already been approved for human use in gene therapy. Actually 12 different AAV serotypes (AAV1 to 12) are known, each with different tissue tropisms. Recombinant AAV are derived from the dependent parvovirus AAV2. The adeno-associated virus type 1 to 12 can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a, site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the protein of interest (i.e., apelin, a variant and the like). Thus, a promoter nucleotide sequence is operably linked to a given DNA sequence if the promoter nucleotide sequence directs the transcription of the sequence.

Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, [beta]-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient to produce a recoverable yield of protein of interest. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Other polypeptides that can be used as APJ receptor agonists include those described in U.S. Pat. No. 6,492,324, in U.S. Pat. No. 7,635,751, in US 2010221255 or in US 2008182779.

In another embodiment, the invention concerns apelinomimetics for use in the treatment or the prevention of a dysfunction associated with aging.

As used herein, the term "apelinomimetics" denotes molecules which are functionally equivalent to apelin that is to say molecules which have at least one of the biological activities of the apelin, such as, for example, hypotensive effect of apelin or plasma glucose lowering of apelin. In other words, "apelinomimetics" denotes molecules able to mimic/reproduce apelin effects.

Activities of apelinomimetics may be determined by any well known method in the art. For example, the capacity of a molecule to be an apelinomimetic may be measured by the capacity to decrease the blood pressure as well as blood glucose like the apelin. The capacity to decrease the blood pressure/glucose of the apelinomimetics of the invention will become evident to the skilled person by implementing a simple test to evaluate the decrease of blood pressure/glucose due to the apelinomimetics.

In another example, apelinomimetics will be evaluated on the ability of apelin inhibitors to block their lowering effects on blood pressure and/or blood glucose.

A further object of the invention relates to pharmaceutical compositions comprising an APJ receptor agonist or an apelinomimetic for use in the treatment or the prevention of a dysfunction associated with aging.

Typically, the APJ receptor agonist or the apelinomimetic may be combined with pharmaceutically acceptable excipients, and optionally sustained-release matrices, such as biodegradable polymers, to form therapeutic compositions.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The APJ receptor agonist or the apelinomimetic can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

A further object of the invention relates to a method for screening drugs for the prevention and treatment of a dysfunction associated with aging comprising the steps consisting of testing a plurality of compounds for their ability to be an APJ receptor agonist or for their ability to be an apelinomimetic, and selecting positively the compounds that are APJ receptor agonists or that are apelinomimetic.

Methods for determining the agonistic activities of a compound for APJ receptors or for determining the activity of apelinomimetics are described above.

Another object of the invention relates to a method for treating a dysfunction associated with aging comprising administering to a subject in need thereof a therapeutically effective amount of an APJ receptor agonist or an apelinomimetic as described above.

In a particular object, the invention relates to a method for treating sarcopenia comprising administering to a subject in need thereof a therapeutically effective amount of an APJ receptor agonist or an apelinomimetic as described above.

In still a particular object, the APJ receptor agonist is the apelin.

As used herein, the term "treating" or "treatment", denotes reversing, alleviating, inhibiting the progress of, or preventing the disorder or condition to which such term applies, or reversing, alleviating, inhibiting the progress of, or preventing one or more symptoms of the disorder or condition to which such term applies.

Method for Predicting Dysfunction Associated with Aging

In a second aspect, the invention relates to an ex vivo method for predicting the ability to a patient to be affected by a dysfunction associated with aging, comprising the step consisting of detecting apelin expression in a sample obtained from said patient.

In a preferred embodiment, the dysfunction associated with aging may be a dysfunction of brain or a dysfunction of muscle.

In another preferred embodiment, the dysfunction of muscle may be a dysfunction a skeletal muscle or cardiac muscle.

In a preferred embodiment, the dysfunction associated with aging may be a sarcopenia.

In another preferred embodiment, the dysfunction associated with aging may be a frailty syndrome Typically, the sample according to the invention may be a blood, plasma, serum, lymph, biopsy or urine sample.

The term "detecting" as used above includes qualitative and/or quantitative detection (measuring levels) with or without reference to a control. Typically apelin expression may be measured for example by RT-PCR or immunohistochemistry'performed on the sample.

The "control" may be a healthy subject, i.e. a subject who does not suffer from any dysfunction associated with aging. The control may also be a subject suffering from dysfunction associated with aging. Preferably, said control is a healthy subject.

Detection of apelin expression in the sample may also be performed by measuring the level of apelin protein. In the present application, the "level of apelin protein" means the quantity or concentration of said apelin protein.

Such methods comprise contacting a sample with a binding partner capable of selectively interacting with apelin protein present in the sample. The binding partner is generally an antibody that may be polyclonal or monoclonal, preferably monoclonal.

The presence of the protein can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound protein in a liquid phase from a solid phase support to which antigen-antibody complexes are bound. Solid supports which can be used in the practice of the invention include substrates such as nitrocellulose (e.g., in membrane or microliter well form); polyvinylchloride (e.g., sheets or microtiter wells); polystyrene latex (e.g., beads or microliter plates); polyvinylidine fluoride; diazotized paper; nylon membranes; activated beads, magnetically responsive beads, and the like.

More particularly, an ELISA method can be used, wherein the wells of a microtiter plate are coated with a set of antibodies against the proteins to be tested. A sample containing or suspected of containing the marker protein is then added to the coated wells. After a period of incubation sufficient to allow the formation of antibody-antigen complexes, the plate(s) can be washed to remove unbound moieties and a detectably labeled secondary binding molecule is added. The secondary binding molecule is allowed to react with any captured sample marker protein, the plate is washed and the presence of the secondary binding molecule is detected using methods well known in the art.

One preferred method utilizes immunohistochemistry, a staining method based on immunoenzymatic reactions using monoclonal or polyclonal antibodies to detect cells or specific proteins such as tissue antigens. Typically, immunohistochemistry protocols involve at least some of the following steps:

1) antigen retrieval (e.g., by pressure cooking, protease treatment, microwaving, heating in appropriate buffers, etc.);
2) application of primary antibody (i.e. anti-apelin protein antibody) and washing;
3) application of a labeled secondary antibody that binds to primary antibody (often a second antibody conjugate that enables the detection in step 5) and wash;
4) an amplification step may be included;
5) application of a detection reagent (e.g. chromagen, fluorescently tagged molecule or any molecule having an appropriate dynamic range to achieve the level of or sensitivity required for the assay);
6) counterstaining may be used and
7) detection using a detection system that makes the presence of the proteins visible (to either the human eye or an automated analysis system), for qualitative or quantitative analyses.

Various immunoenzymatic staining methods are known in the art for detecting a protein of interest. For example, immunoenzymatic interactions can be visualized using different enzymes such as peroxidase, alkaline phosphatase, or different chromogens such as DAB, AEC, or Fast Red; or fluorescent labels such as FITC, Cy3, Cy5, Cy7, Alexafluors, etc. Counterstains may include H&E, DAPI, Hoechst, so long as such stains are compatible with other detection reagents and the visualization strategy used. As known in the art, amplification reagents may be used to intensify staining signal. For example, tyramide reagents may be used. The staining methods of the present invention may be accomplished using any suitable method or system as would be apparent to one of skill in the art, including automated, semi-automated or manual systems.

The method of the invention may comprise a further step consisting of comparing the apelin expression level with a threshold value.

Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. Preferably, the person skilled in the art may compare the apelin expression level obtained according to the method of the invention with a defined threshold value.

Preferably, said threshold value is the mean apelin expression level of a population of healthy individuals, preferably of individuals known to be healthy, i.e. which are not in a critical situation, and preferably which do not suffer from dysfunction associated with aging.

Typically, the skilled person in the art may determine the apelin expression level in a biological sample of a statistical sample from the population of individuals known to be healthy, preferably 100 healthy individuals. The mean value of the obtained levels is then determined, according to well known statistical analysis, so as to obtain the mean level of apelin expression. Said value is then considered as being normal and thus constitute a threshold value.

By comparing the apelin expression level to this threshold value, the physician is then able to predicting dysfunction associated with aging. Accordingly, the physician would be able to adapt and optimize appropriate medical care of a subject in a critical and life-threatening condition suffering from dysfunction associated with aging. The determination of said prediction is highly appropriate for follow-up care and clinical decision making.

Therefore, the invention relates to a method for predicting the ability to a patient to be affected by a dysfunction associated with aging, said method comprising the following steps:

a) determining the apelin expression level in a biological sample of said subject;

b) determining the mean level of apelin expression in a biological sample of a population of healthy individuals, preferably 100 healthy individuals; and c) a step of comparing the ratio obtained in a) to the ratio obtained in b).

The present invention also relates to kits for the predicting of dysfunction associated with aging, comprising means for detecting apelin expression.

According to the invention, the kits of the invention may comprise an anti-apelin protein antibody; and another molecule coupled with a signalling system which binds to said apelin protein antibody.

Typically, the antibodies or combination of antibodies are in the form of solutions ready for use. In one embodiment, the kit comprises containers with the solutions ready for use. Any other forms are encompassed by the present invention and the man skilled in the art can routinely adapt the form to the use in immunohistochemistry.

The present invention also relates to apelin as a biomarker for dysfunction associated with aging.

The invention will be further illustrated by the following figures and examples. However, these examples and figures should not be interpreted in any way as limiting the scope of the present invention.

FIGURES

Figure 1:
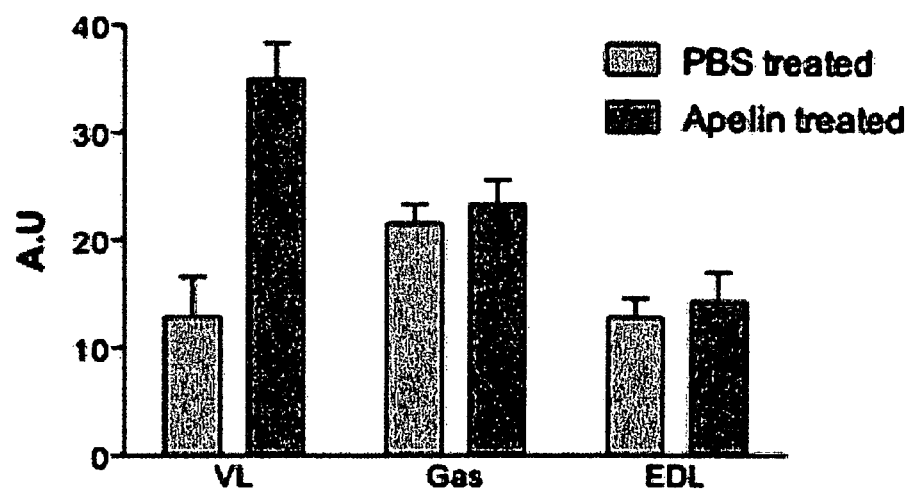
Figure 1:
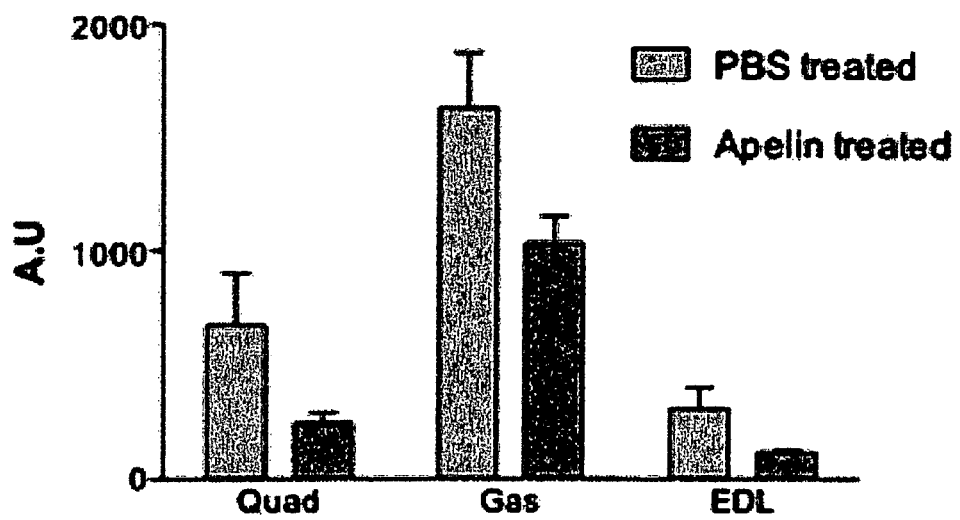
Figure 1:
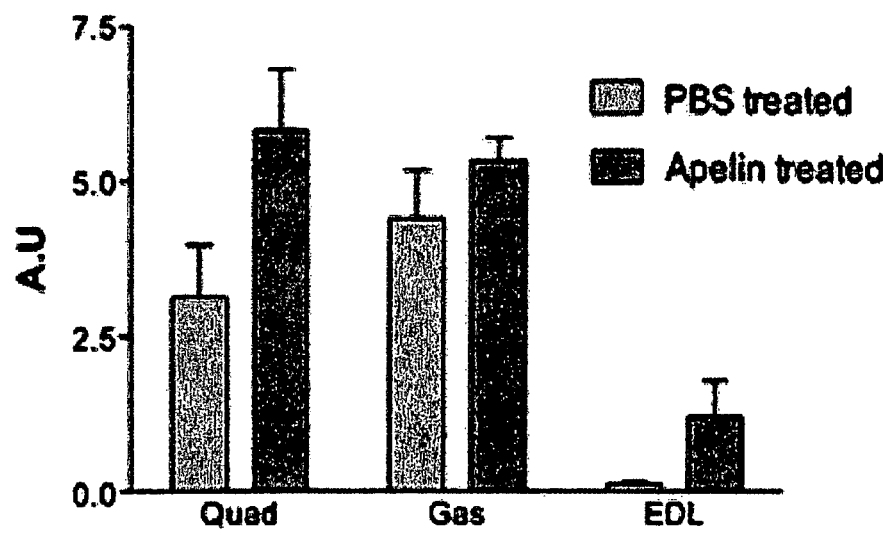
Figure 1:
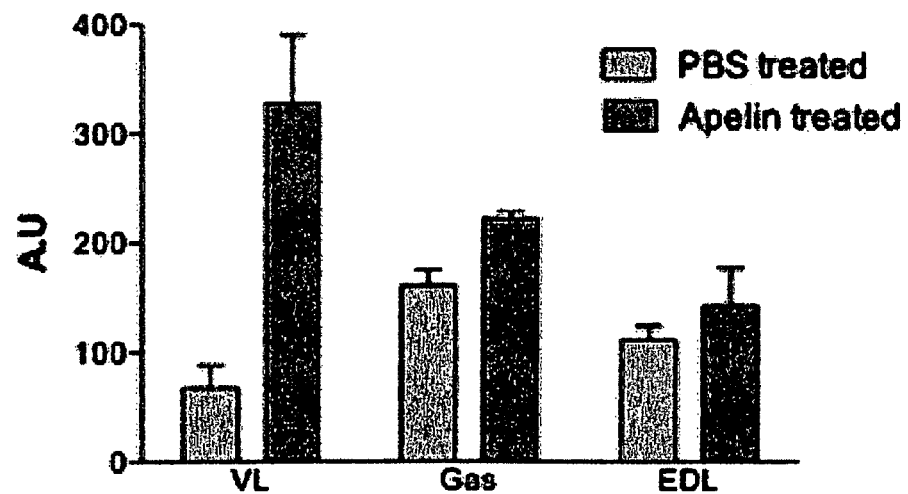

FIGS. 1A and B: Consequences of a chronic apelin treatment on muscle genes expression.

Mice were treated or not with apelin (0.1 µmole/kg/day) or with PBS (control) during 28 days. After euthanasia each muscle was rapidly frozen in liquid nitrogen. mRNA expression was quantified as described in Material and Methods.

Figure 2:
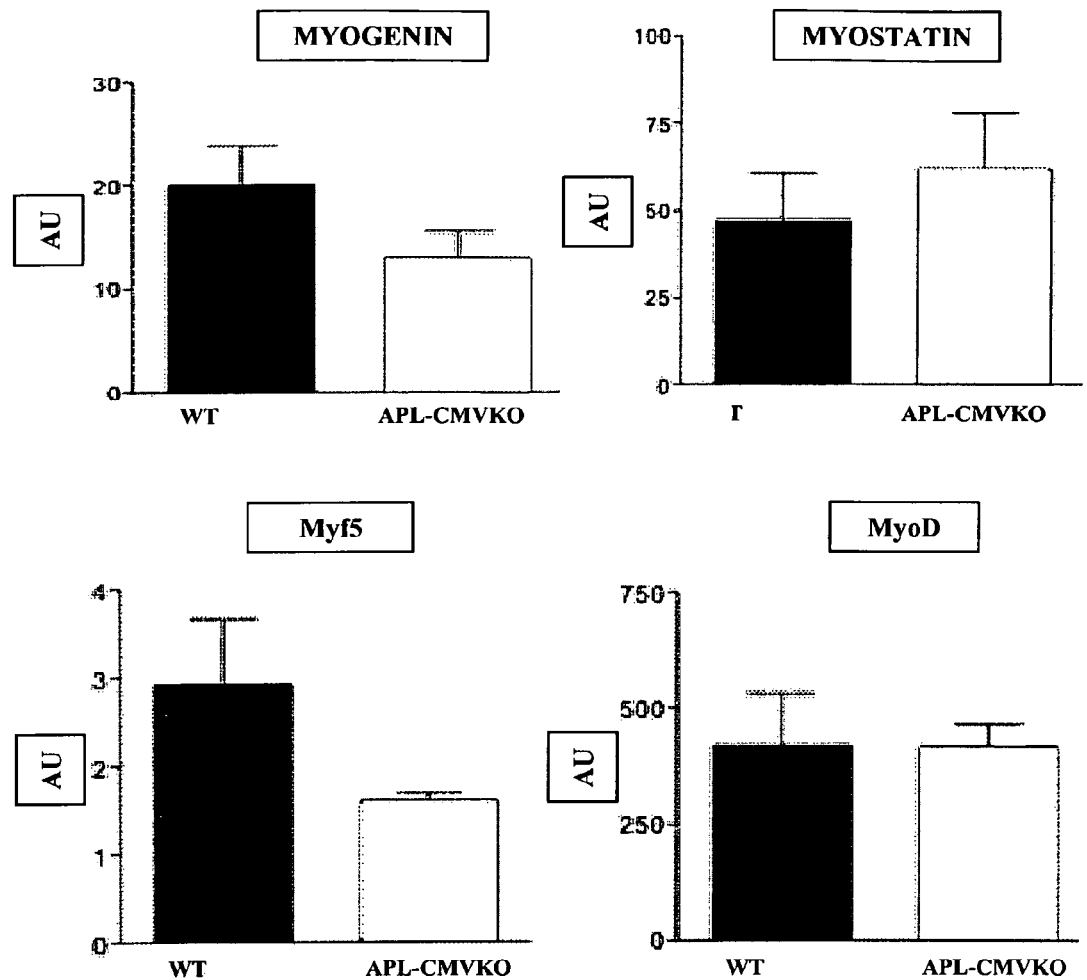

FIG. 2: Muscular mRNA expression of factors involved in myogenesis in 80 week-aged WT or CMV-KO Apelin mice.

After 80 weeks, mice were euthanasied and quadriceps muscle was rapidly frozen in liquid nitrogen. mRNA expression was quantified as described in Material and Methods.

Figure 3:
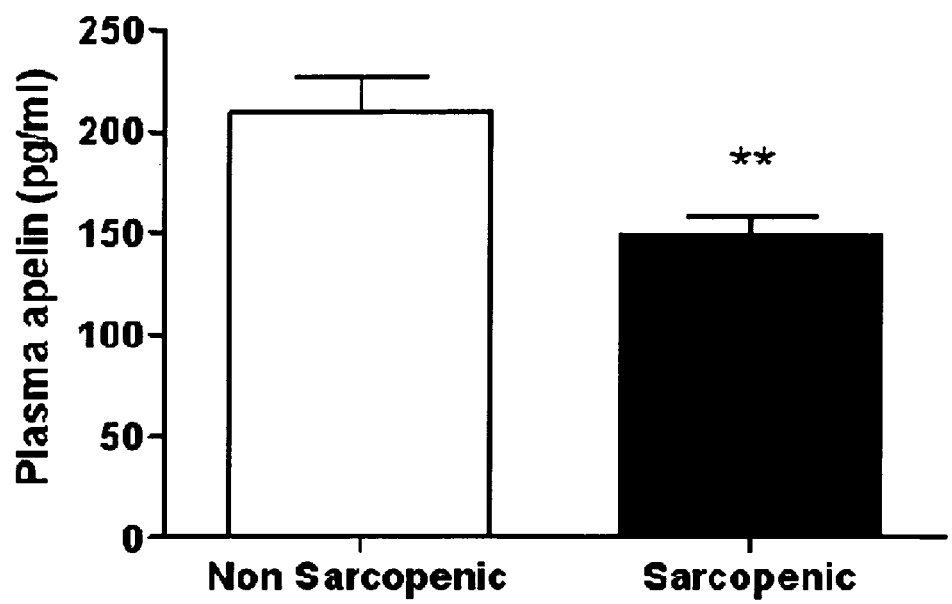

FIG. 3: Plasma apelin variation in sarcopenic individuals.

Figure 4:
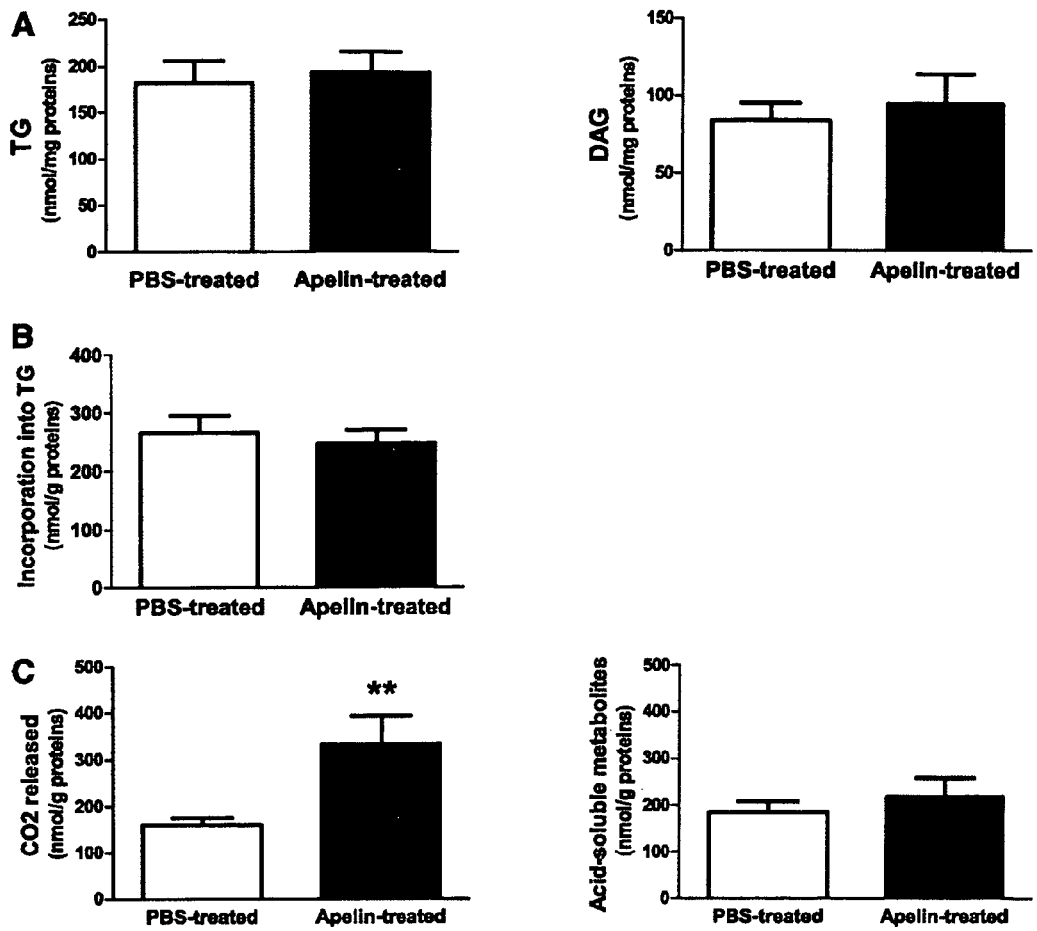

FIG. 4: Effect of chronic apelin treatment on palmitate partitioning in muscle of insulin-resistant mice.

A: TG and DAG levels in muscle homogenates of PBS-treated (n=7) and apelin-treated (n=8) mice. Results are means±SEM. B: Measure of [14C]palmitate incorporation into TG in muscle of PBS-treated (n=11) and apelin-treated (n=12) mice. Results are means±SEM. C: Complete (left) and incomplete (right) FAO measured as described in research design and methods. Results are means±SEM of PBS-treated (n=11) and apelin-treated (n=9) mice. **P≤0.01.

FIG. 5: Chronic apelin treatment in HFD mice increased mitochondrial oxidative capacities and biogenesis in muscle.

A: State 2 and State 3 respiration were measured on fresh permeabilized fibers prepared from soleus skeletal muscle of PBS-treated (n=7) and apelin-treated. (n=7) mice as described in research design and methods. B: Representative Western blot of the different mitochondrial complexes (left) and quantification (right) in PBS-treated (n=6) and apelin-treated (n=7) mice. Results are means±SEM. *P≤0.05. C: Gene expression in soleus muscle of PBS-treated (n=5) and apelin-treated (n=5) mice. Results are means±SEM. *P≤0.05. D: mtDNA quantity calculated as the ratio of COX1 to cyclophilin A DNA levels determined by real-time PCR in soleus of PBS-treated (n=4) and apelin-treated (n=4) mice. **P≤0.01. E: Transmission electron microscopy images at magnification ×6,000 and ×25,000 in SS and IMF mitochondria (left). Quantification of mitochondria number relative to the section area (analysis of three images for each mouse) from soleus of PBS-treated (n=4) and apelin-treated (n=5) mice (right).

FIG. 6: The effects of apelin on FAO and mitochondrial biogenesis in muscle are dependent on AMPK activation.

A: Phospho-AMPK and phospho-ACC protein expression after PBS (n=3) or apelin (n=4) treatment in muscle of insulin-resistant mice. The graph shows the quantified data (n=4). B: Malonyl-CoA concentration in soleus muscle of PBS-treated (n=6) or apelin-treated (n=6) mice. C: Total FAO measured as described in research design and methods in HFD PBS- and apelin-treated WT and AMPK-DN mice. Results are means±SEM; n=4 in each group. D: mtDNA quantity calculated as the ratio of COX1 to cyclophilin A DNA levels determined by real-time PCR in soleus of the different mice; n=4 in each group. E: Gene expression in soleus muscle of PBS- and apelin-treated WT and AMPK-DN mice. Results are means±SEM; n=4 in each group. *P≤0.05. **P≤0.01.

Figure 7:
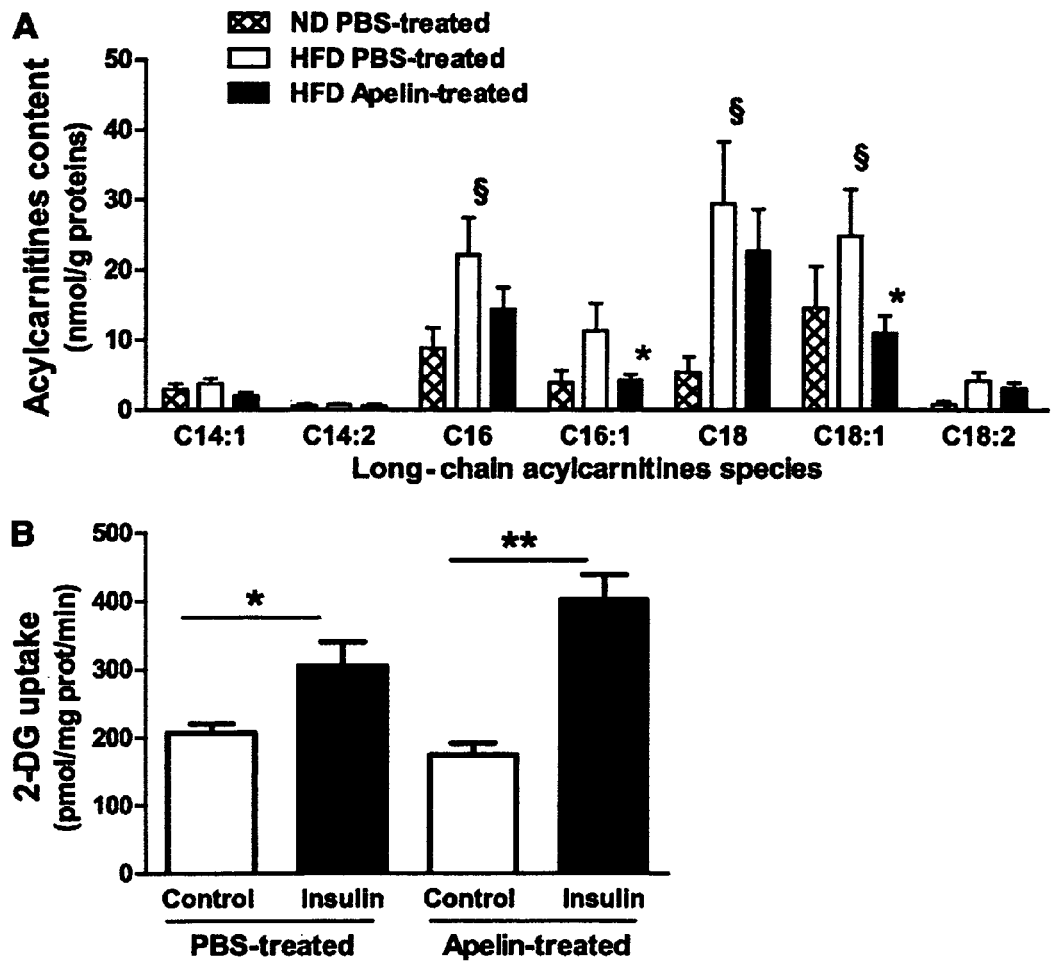

FIG. 7: Effect of chronic apelin treatment in muscle of insulin-resistant mice on acylcarnitine levels and insulin-stimulated glucose uptake.

A: Long-chain species acylcarnitine levels were measured in ND-fed mice (n=5) and in HFD-fed mice treated with apelin (n=8) or PBS (n=7). Results are means±SEM. *P≤0.05. B: Insulin-induced glucose uptake in soleus muscle of PBS-treated (n=7) and apelin-treated (n=6) mice. Results are means±SEM. *P≤0.05, **P≤0.01. 2-DG, 2-deoxyglucose; Prot, protein.

EXAMPLES

Examples 1

Material & Methods

Animals.

Mice were handled in accordance with the principles and guidelines established by the National Institute of Medical Research (INSERM). C57B16/J wild type mice were obtained from Harlan (Gannat, France). CMV-KO apelin mice were obtained from Genoway (Lyon, France). Mice were housed conventionally in a constant temperature (20-22° C.) and humidity (50-60%) animal room, with a 12/12 h light/dark cycle (lights on at 8:00 am) and free access to food and water. The mice were fed a chow diet from weaning until 10-week-old and then either maintained on a chow diet (Research Diet, NJ).

Apelin Treatment.

Apelin treatment was processing to mice from 31 weeks old to 35 weeks old. Mice were daily injected with intraperitoneal injection of apelin (0.1 µmole/kg/day) as previously described (Higuchi et al 2005; Yue et al 2010) for 28 days. Age-matched control mice were PBS-injected during the same period. All mice were sacrificed 24 h after the last apelin ip injection in a fed state. Plasma apelin concentrations, measured after a bolus of ip apelin (0.1 µmole/kg), were increased just over 2.5 fold 10 min after injection.

Real-Time PCR.

Total RNAs (1 mg) were isolated from muscles using GeneJET RNA Purification Kit (Fermentas, USA). Total RNAs were reverse transcribed using random hexamers and Superscript 11 reverse transcriptase (Invitrogen, UK). Real time PCR was performed as previously described (Boucher et al. 2005).

Results
1. Apelin Treatment
1°) Myostatin

TABLE 1 quantification of Myostatin marker in mice treated with apelin

| | PBS-treated | | | | | | | Apelin-treated | | |
|---|---|---|---|---|---|---|---|---|---|---|
| Quad | 1510.00 | 412.20 | 130.80 | 732.50 | 584.90 | 218.300 | 381.700 | 90.100 | 263.400 | 268.000 |
| Mean | | | 674.080 | | | | | 244.300 | | |
| SEM | | | 231.7178 | | | | | 47.04195 | | |
| Gas | 1115.40 | 1465.30 | 2108.70 | 1190.50 | 2291.40 | 1058.400 | 606.000 | 1287.900 | 1009.300 | 1208.40 |
| Mean | | | 1634.260 | | | | | 1034.000 | | |
| SEM | | | 239.9596 | | | | | 118.1673 | | |
| EDL | 222.40 | 139.00 | 314.00 | 660.90 | 188.00 | 137.800 | 114.600 | 94.600 | 92.900 | 133.40 |
| Mean | | | 304.860 | | | | | 114.660 | | |
| SEM | | | 93.49157 | | | | | 9.38763 | | |

2°) Myogenin

TABLE 2 quantification of myogenin marker in mice treated with apelin

| | PBS-treated | | | | | Apelin-treated | | | |
|---|---|---|---|---|---|---|---|---|---|
| Quad | 7.0 | 18.8 | 6.0 | 19.8 | 40.7 | 30.2 | 29.2 | 29.5 | 45.7 |
| Mean | | 12.900 | | | | | 35.060 | | |
| SEM | | 3.7063 | | | | | 3.419737 | | |
| Gas | 16.6 | 21.3 | 23.1 | 25.3 | 30.6 | 19.6 | 20.2 | 19.6 | 26.8 |
| Mean | | 21.575 | | | | | 23.360 | | |
| SEM | | 1.849042 | | | | | 2.263979 | | |
| EDL | 15.0 | 8.2 | 16.1 | 11.9 | 24.1 | 1.3 | 16.1 | 9.4 | 10.5 |
| Mean | | 12.800 | | | | | 14.280 | | |
| SEM | | 1.772475 | | | | | 2.708579 | | |

3°) MyoD

TABLE 3 quantification of MyoD marker in mice treated with apelin

| | PBS-treated | | | | | Apelin-treated | | | |
|---|---|---|---|---|---|---|---|---|---|
| Quad | 53.4 | 127.6 | 52.6 | 36.5 | 565.9 | 202.2 | 293.8 | 293.0 | 285.9 |
| Mean | | 67.525 | | | | | 328.160 | | |
| SEM | | 20.39981 | | | | | 61.88255 | | |
| Gas | 142.4 | 137.8 | 163.1 | 198.9 | 228.1 | 222.0 | 202.9 | 219.9 | 238.6 |
| Mean | | 160.550 | | | | | 222.300 | | |
| SEM | | 13.91704 | | | | | 5.837553 | | |
| EDL | 128.4 | 90.6 | 136.8 | 88.8 | 220.9 | 230.7 | 79.3 | 92.1 | 89.6 |
| Mean | | 111.150 | | | | | 142.520 | | |
| SEM | | 12.5077 | | | | | 34.10176 | | |

4°) Myf5

TABLE 4 quantification of Myf5 marker in mice treated with apelin

| | PBS-treated | | | | | Apelin-treated | | | |
|---|---|---|---|---|---|---|---|---|---|
| Quad | 3.7 | 5.1 | 2.6 | 1.1 | 7.5 | 8.7 | 3.7 | 5.2 | 4.0 |
| Mean | | 3.125 | | | | | 5.820 | | |
| SEM | | 0.8469307 | | | | | 0.9825477 | | |
| Gas | 6.5 | 4.6 | 2.8 | 3.7 | 6.1 | 5.6 | 5.0 | 5.9 | 4.1 |
| Mean | | 4.400 | | | | | 5.340 | | |
| SEM | | 0.7905694 | | | | | 0.3613862 | | |
| EDL | 0.2 | 0.1 | 0.1 | 0.1 | 1.3 | 0.2 | 3.3 | 0.1 | 1.1 |
| Mean | | 0.125 | | | | | 1.200 | | |
| SEM | | 0.025 | | | | | 0.5761944 | | |

II. CMV-KO Apelin

TABLE 5 quantification of markers in KO apelin mice

| | CMV-KO Ape 80 week old | | | WT 80 week old | | |
|---|---|---|---|---|---|---|
| Myostatin | 35.9000 | 58.7300 | 91.57 | 72.1400 | 43.6300 | 25.20 |
| Mean | | 62.07 | | | 46.99 | |
| SEM | | 27.98 | | | 23.65 | |
| Myogenin | 15.5500 | 15.6000 | 7.83 | 12.5600 | 22.3500 | 25.22 |
| Mean | | 12.99 | | | 20.04 | |
| SEM | | 4.472 | | | 6.638 | |
| MyoD | 429.3500 | 330.4800 | 493.22 | 208.7100 | 584.6100 | 468.17 |
| Mean | | 417.7 | | | 420.5 | |
| SEM | | 81.99 | | | 192.4 | |
| Myf5 | 1.6200 | 1.7500 | 1.44 | 1.4600 | 3.8500 | 3.46 |
| Mean | | 1.603 | | | 2.923 | |
| SEM | | 0.1557 | | | 1.282 | |

Conclusion

The FIGS. 1A and B clearly demonstrate that apelin treatment increased myogenic markers expression such as Myogenin, MyoD and Myf 5 in quadriceps muscles of moderate aged-mice. In parallel, this 28-days treatment was also able to decrease myostatin expression in these muscles confirming a benefic role of apelin in myogenesis.

The FIG. 2 shows that apelin deletion in mouse (APL-CMVKO) promotes a decrease of myogenic markers (myogenin and Myf5) in mouse quadriceps accompanied by a slight increase of myostatin, a marker of sarcopenia in muscle (see Kate T. Murphy, Rene Koopman, Timur Naim, Bertrand Léger, Jennifer Trieu, Chilcwendu Ibebunjo, and Gordon S. Lynch. Antibody-directed myostatin inhibition in 21-mo-old mice reveals novel roles for myostatin signaling in skeletal muscle structure and function. The FASEB Journal 0892-6638/10/0024-4433).

Taken together, these results demonstrate that apelin is involved in myogenic processes and could be a potential target to fight aging associated dysfunctions.

Example 2

Material and Methods

Apelin has been measured in simple blind test by commercial ELISA kit (Phoenix Pharmaceutical Inc., USA) in plasma from old individuals diagnosed for sarcopenia according to the Newman's index (n=30) or old individual healthy (n=30). This index takes into consideration the appendicular muscular mass and the fat mass. Four quartiles of individuals have been done according to their Newman's index and extreme quartiles have been selected to determine sarcopenic or no-sarcopenic state.

Results and Discussion

FIG. 3 shows that plasma apelin levels are significantly decreased in sarcopenic individuals (humans). This decrease is not correlated with body mass index or insulin suggesting that plasma apelin level could be considered as a strong biomarker of age-associated muscular diseases.

Example 3

Effect of Apelin on Muscle Metabolism

Material and Methods

Mice were handled in accordance with the principles and guidelines established by INSERM. C57B16/J wild-type (WT) mice were obtained from Harlah (Gannat, France). Mice with muscle-specific inactive AMPK (AMPK-DN mice) were provided by Prof. Moris J. Birnbaum (Howard Hughes Medical Institute, University of Pennsylvania, Philadelphia, Pa.). Apelin-deficient (apelin−/−) mice were generated as described previously (10) and backcrossed to C57B16/J mice >10 times. Mice were housed conventionally in a constant temperature (20-22° C.) and humidity (50-60%) animal room, with a 12/12 h light/dark cycle (lights on at 7:00 a.m.) and free access to food and water. The C57B16/J and AMPK-DN mice were fed an ND from weaning until aged 10 weeks and then either maintained on ND (control group) or fed an HFD containing 20% protein, 35% carbohydrate, and 45% fat (Research Diets, New Brunswick, N.J.). Apelin treatment began after the onset of insulin resistance in males aged 23 weeks. Mice were injected daily with apelin-13 (Phoenix Biotech) at 0.1 mmol/kg/day i.p. as previously described (7) for 28 days. Age-matched control mice were PBS injected during the same period. Standard mice were also treated with a specific APJ receptor antagonist (F13A) (Phoenix Biotech) (11) at 0.2 µmol/kg/day during 28 days or with the combination of apelin and F13A. All mice were killed 24 h after the last apelin injection in a fed state. Plasma apelin concentrations, measured after a bolus of apelin (0.1 µmol/kg i.p.) in HFD mice, were increased >2.4-fold 10 min after injection (4.12±0.96 vs. 1.73±0.24 ng/mL before the injection, n=5), but plasma apelin concentrations were not different between PBS- and apelin-treated mice at the end of the treatment.

Plasma Measures.

Plasma fatty acids (FM) and TGs measured by colorimetric technique with the Wako NEFA kit (Wako Chemicals) and the PAP 150 Kit (bioMerieux), respectively, as well as plasma leptin, adiponectin (Quantikine; R&D Systems), and apelin (Phoenix Pharmaceuticals, Inc.), were determined in the fed state at the end of the treatment. Insulinemia (Mercodia, Uppsala, Sweden) and glycemia measured with a glucometer (Accu-check; Roche Diagnostics) were determined in the fasted state on blood from the tail vein.

Palmitate Oxidation and Esterification.

Palmitate oxidation was determined as previously described in whole soleus muscle or adipose tissues (12). The tissues were incubated in modified Krebs-Henseleit buffer containing 1.5% FA-free BSA, 5 mmol/L glucose, 1 mmol/L palmitate, and 0.5 µCi/mL [14C]palmitate (PerkinElmer) for 60 min. At the end of the incubation, tissues were removed and homogenized in 800 µL lysis buffer. Complete oxidation was determined by acidifying the incubation buffer with 1 mL of 1 mol/L H2SO4, and the 14CO2 was trapped by benzethonium hydroxide (Sigma-Aldrich) placed in a 0.5 mL microtube in a sealed glass vial. After 120 min, the microtube was removed and placed in a scintillation vial, and the radioactivity was counted (Cytoscint; MP Biomedicals). A total of 500 µL homogenate was placed into glass tubes to extract lipids with chloroform-methanol (2:1) and 2 mol/L KCl—HCl. After centrifugation, the aqueous phase (500 µL) was quantified by liquid scintillation to determine the acid-soluble metabolites production (incomplete oxidation) and the organic phase (200 µL) used to measure palmitate esterification as previously described (12).

O2 Consumption Measurement on Mitochondria.

O2 consumption was measured on fresh permeabilized fibers prepared from soleus muscle using a respirometer (Oxygraph-2k; OROBOROS INSTRUMENTS, Innsbruck, Austria) as previously described (13,14). First, a 20 mmol/L glutamate per 4 mmol/L malate mixture was injected to assess the complex I activity (gmState 2). Complex I was then blocked by addition of 5 µmol/L rotenone. Thereafter, 10 mmol/L succinate was added to access the complex II activity (sState 2). State 3 of respiration was obtained after further addition of 10 mmol/L ADP. O2 consumption for each state was calculated using DataGraph software.

Transmission Electron Microscopy.

Soleus muscle was cut into small pieces and fixed as previously reported (15). The tissue was then cut and mounted on copper grids and observed with a Hitachi HU 12A transmission electron microscope equipped with a high-resolution camera. The pictures obtained were analyzed with Lucia G software.

Mitochondrial DNA Analysis.

Total DNA was extracted from soleus muscle using a commercial kit (DNeasy; QIAGEN). The content of mitochondrial (mt)DNA was calculated using real-time quantitative PCR by measuring the threshold cycle ratio of a mitochondrial encoded gene (COX1) and a nuclear-encoded gene (cyclophilin A) as previously described (15).

Determination of Skeletal Muscle Acylcarnitines, Diacylglycerol, and TG Levels Acylcarnitines.

Part of muscle homogenate (20 µL) was spotted on, filter membranes (Protein Saver 903 cards; Whatman). The dried spots were then treated as reported (17). In brief, acylcarnitines were derivatized by addition of butanolic HCl and treated with the reagents of the NeoGram MSMS-AAAC kit (PerkinElmer). Free carnitine and acylcarnitines were quantified by liquid chromatography-tandem mass spectrometry. Data were acquired using a Micromass Quattro Micro API spectrometer equipped with a 2795 high-performance liquid chromatography module and a data system controlled by MassLynx 4.1 operating system (Waters, Milford, Mass.).

Neutral Lipids (Diacylglycerol and TG).

Muscles (5-10 mg) were homogenized in 2 mL methanol per 5 mmol/L EGTA (2:1 v/v) with FAST-PREP (MP Biomedicals). A total of 100 µL was evaporated, the dry pellets were dissolved in 0.1 mL NaOH (0.1 mol/L) overnight, and proteins were measured with the Bio-Rad assay. Neutral lipids corresponding to 0.9 mL of the homogenate were extracted according to Bligh and Dyer (18) in chloroform/methanol/water (2.5:2.5:2.1 v/v/v) in the presence of the internal standards and measured as previously described (19).

Malonyl-CoA Assay.

Malonyl-CoA levels were measured on frozen soleus muscle as previously described (20). In brief, muscle were homogenized (10 mg tissue in 250 µL, phosphate buffer containing 1 mol/L KPO4 and 10 mmol/L EDTA, pH 7.0) on ice with a potter and then centrifuged. Supernatant (100 µL) was then incubated for 1 h at 37° C. with assay buffer (phosphate buffer with 2.5 mmol/L dithiothreitol, 0.2 mmol/L NADPH, 0.01% free FA BSA, 13 µmol/L acetyl-CoA, and 0.63 µCi 3H-acetyl-CoA) (PerkinElmer), and 25 mU of FA synthetase (provided by Prof. Marc Prentki, Centre Hospitalier de l'Université de Montréal Research Centre, Montreal, Ontario, Canada). The reaction stopped with 25 µL perchloric acid, and then ethanol and petroleum acid was added. A total of 4 mL of the upper phase was transferred in a new tube containing 2 mL water, and after centrifugation, 3 mL of the upper phase was dried and radioactivity was measured after addition of 10 mL scintillation liquid.

Western Blot Analysis.

Western blot analyses were performed as previously described (4) by loading samples (lysed muscle) on 4-12% Criterion/XT gel (Bio-Rad) and transferring to nitrocellulose membranes (Schleicher & Schuell Bioscience) that had been probed with antiphospho-AMPK-α (Thr172), antiphospho-acetyl-CoA carboxylase (ACC) (Ser79) (Cell Signaling Technology, Beverly, Mass.), or anti-OxPhos antibodies (MitoSciences, Mundolsheim, France) used at 1/1,000 dilution. Membranes were probed with β-actin or AMPK or ACC antibodies for total proteins.

Protein Assay.

Concentration of samples was determined using the DC protein assay kit (Bio-Rad) according to the manufacturer's instructions.

Real-Time PCR.

Total RNAs (1 µg) were isolated from muscle using RNA STAT (AMS Technology, Lutterworth, U.K.) and were reverse transcribed using random hexamers and Superscript II reverse transcriptase (Invitrogen, Paisley, U.K.). Real time PCR was performed as previously described (1). Analysis of the 18S ribosomal RNA was performed using the ribosomal RNA control TaqMan Assay Kit (Applied Biosystems) to normalize gene expression.

Glucose Uptake.

Muscles were isolated and preincubated for 10 min in Krebs-Henseleit buffer (pH 7.4) containing 2 mg/mL BSA, 2 mmol/L sodium pyruvate, and 20 mmol/L HEPES. Muscles were then incubated for 45 min in the absence or presence of 100 nmol/L insulin as previously reported (4).

Statistical Analysis.

Data are presented as means±SEM. Comparisons between groups were carried out for different parameters using Prism 5.0 software (GraphPad Software). A two-way ANOVA was applied to detect interaction between treatment and time. When appropriate, Student t test paired or nonpaired was applied. Differences at P≤0.05 were considered statistically significant.

Results and Discussion

Effect of Chronic Apelin Treatment in HFD (High-Fat Diet) Mice on Skeletal Muscle Lipid Metabolism Ex Vivo.

Apelin treatment in HFD mice does not reduce the amount of IMTG and DAG when compared with PBS treatment (FIG. 4A). Apelin treatment also has no effect on the rate of palmitate incorporation into TG (FIG. 4B). To further investigate the fates of lipids, both complete and incomplete oxidation of [14C]palmitate were assessed. Chronic apelin treatment significantly increased complete oxidation of [14C]palmitate to $CO_2$ in soleus muscle when compared with PBS treatment (FIG. 4C). Of interest, incomplete oxidation was not significantly increased by chronic apelin treatment (FIG. 4C). Moreover, in soleus of HFD apelin−/− mice, the complete oxidation was not increased (243.5±9.6 vs. 198.4±59.9 nmol $CO_2$ released per gram protein in apelin−/− mice, n=3-4). Altogether, these results show that apelin treatment promotes complete FAO (fatty acid oxidation) in skeletal muscle of obese and insulin-resistant mice.

Effect of Chronic Apelin Treatment in HFD Mice on Muscle Mitochondrial Activity and Density.

To get further insight toward the effect of apelin, mitochondrial respiration was first assessed on freshly permeabilized muscle fibers. No difference in the glutamate/malate-driven mitochondrial respiration was found between PBS- and apelin-treated mice, suggesting that the complex I activity was not affected by the apelin treatment (data not shown). However, the succinate-driven mitochondrial respiration was significantly higher in fibers from apelin-treated mice compared with control, suggesting an increase in the oxidative capacity from complex II that uses coenzymes derived from FAO (FIG. 5A). The succinate and adenylate-driven respiration was also significantly higher in apelin-treated mice, indicating that the capacity of the oxidative phosphorylation was increased in soleus after apelin treatment. Protein expression of complex II, III, and V also was significantly increased in apelin-treated mice (FIG. 5B). In addition, an increased citrate synthase activity, a quantitative marker of mitochondria content, was also found in muscle homogenates of apelin-treated mice compared with control (2.62±0.02 vs. 2.91±0.07 µmol/min/mg proteins, n=7-9; P<0.001). Expression of peroxisome proliferator-activated receptor γ coactivator 1-α (PGC1-α), a transcriptional coactivator mediating mitochondrial biogenesis, was also significantly increased in muscle of apelin-treated mice, whereas expression of PGC1-β was not modified (FIG. 5C). Moreover, expression of nuclear respiratory factor 1 (NRF1) and mitochondrial transcription factor A (TFAM), which act in concert to increase mitochondrial oxidative phosphorylation and mitochondrial biogenesis, were also upregulated. Altogether, these results strongly suggest that in response to apelin treatment, mitochondrial biogenesis was increased in skeletal muscle from insulin-resistant mice. To test this hypothesis, we measured muscle mtDNA and density. The mtDNA-to-nuclear DNA ratio was significantly higher in soleus muscle of apelin-treated mice than in PBS-treated mice (FIG. 5D). Moreover, the electron microscopy demonstrated that apelin treatment significantly increased the density of intramyofibrillar (IMF) mitochondria (FIG. 5E), the largest fraction of the total mitochondria content. Fewer adverse alterations of mitochondria ultrastructure (reduced electron density of the matrix and loss of cristae) also were observed in both IMF and subsarcolemmal (SS) mitochondria of soleus muscle of apelin-treated mice (FIG. 5E), strengthening the effect of apelin on mitochondria function and biogenesis.

To study more deeply the apelin mechanism of action, the involvement of APJ receptor in apelin effects was first determined. For this purpose, mice were treated during the same period with either apelin alone or apelin and a specific APJ receptor antagonist (F13A) F13A antagonist behaved as a functional antagonist. In muscle of F13A/apelin-treated mice, FAO and mitochondrial biogenesis were abrogated compared with apelin-treated mice (data not shown), indicating that apelin exerts its beneficial effects through APJ activation.

Next, the role of AMPK in mediating the effects of apelin was investigated since apelin is known to activate AMPK in skeletal muscle and AMPK is involved in both FAO and mitochondrial biogenesis. Apelin treatment significantly increased both AMPK and ACC phosphorylation in muscle of insulin-resistant mice (FIG. 6A). The inhibition of ACC activity (as a result of increased phosphorylation) had for consequence a significant reduction of malonyl-CoA concentrations in muscle of apelin-treated mice (FIG. 6B). In addition, the increased FAO and mitochondrial biogenesis observed in HFD WT apelin-treated mice was completely blunted in muscle of HFD AMPK-DN apelin-treated mice, and the overexpression of PGC1-α, TFAM, and NRF1 was reduced (FIG. 6C-E). Thus, AMPK is a direct target of apelin and is required for apelin effect on FAO and mitochondrial biogenesis.

Chronic Apelin Treatment in HFD Mice Improves Muscle Insulin Sensitivity.

Acylcarnitines represent by-products of substrate catabolism arising from incomplete FAO. Increased acylcarnitine levels have been shown to be associated with obesity and insulin resistance. Long-chain acylcarnitines were elevated in homogenates of soleus muscle from HFD insulin-resistant mice compared with ND control mice (FIG. 7A). It is interesting that in HFD apelin-treated mice, acylcarnitine levels, especially C16:1 and C18:1 species, were reduced when compared with HFD PBS-treated mice. Since chronic apelin treatment increased complete but not incomplete FAO in soleus, we hypothesized that the resulting lower levels of acylcarnitines would correlate with improved insulin sensitivity in muscle. Indeed, insulin-stimulated glucose uptake was significantly increased in apelin-treated mice muscle compared with PBS-treated mice (FIG. 7B).

Conclusion:

The inventors show that chronic apelin treatment increases complete FAO, mitochondrial respiratory capacity, and mitochondrial biogenesis in skeletal muscle of insulin-resistant mice. The influx of lipid in mitochondria was associated with decreased acylcarnitine levels, suggesting a tighter coupling between FAO and the tricarboxylic acid cycle. Such a tighter coupling appears important to improve insulin sensitivity since increased insulin-stimulated glucose transport in muscle of apelin-treated mice is observed. Increased FAO and mitochondrial biogenesis in muscle and decreased total adiposity could contribute to the overall improvement of insulin sensitivity observed with chronic apelin treatment.

Chronic apelin treatment triggers an amelioration of both lipid and glucose metabolism. Chronic apelin treatment optimizes muscle mitochondrial performance through increased mitochondrial biogenesis and a tighter matching between FAO and the tricarboxylic acid cycle. Thus, APJ receptor agonist like apelin or an apelinomimetic should be used in the treatment or the prevention of disease associated problems in energetic mechanism in mitochondria like a dysfunction associated with aging and more particularly in the treatment or prevention of dysfunction of skeletal muscle (like sarcopenia) or cardiac muscle.

The invention claimed is:

1. A method for treating sarcopenia comprising administering to a subject in need thereof a therapeutically effective amount of an APJ (apelin) receptor agonist, wherein the APJ receptor agonist is selected from the group consisting of apelin, a polypeptide and a small organic molecule.

* * * * *